United States Patent [19]

Moro et al.

[11] Patent Number: 5,223,244

[45] Date of Patent: Jun. 29, 1993

[54] AEROSOL COMPOSITION

[75] Inventors: Osamu Moro; Toshihiko Nakane; Shuya Tamaki; Tsunehiko Iwai, all of Yokohama, Japan

[73] Assignee: Shiseido Company, Ltd., Tokyo, Japan

[21] Appl. No.: 627,073

[22] Filed: Dec. 13, 1990

Related U.S. Application Data

[63] Continuation-in-part of Ser. No. 366,836, Jun. 15, 1989, abandoned.

[30] Foreign Application Priority Data

Jun. 20, 1988 [JP] Japan .................................. 63-150194
Oct. 11, 1988 [JP] Japan .................................. 63-255401

[51] Int. Cl.$^5$ ................................... A61K 9/14
[52] U.S. Cl. ..................................... 424/46; 424/45; 252/305; 252/306
[58] Field of Search ................. 252/8, 2, 305; 424/45, 424/46, 47, 43, 68, 67, 66

[56] References Cited

U.S. PATENT DOCUMENTS

| | | | |
|---|---|---|---|
| 3,494,871 | 2/1970 | Clapp et al. | 252/188.3 |
| 3,863,005 | 1/1975 | Mace et al. | 424/45 |
| 4,018,887 | 4/1977 | Danneman et al. | 424/47 |
| 4,025,615 | 5/1977 | Rubino | 424/46 |
| 4,152,416 | 5/1979 | Spitzer et al. | 424/46 |
| 4,174,295 | 11/1979 | Bargigia et al. | 252/305 |
| 4,243,548 | 1/1981 | Heeb et al. | 424/45 |
| 4,328,319 | 5/1982 | Osipow et al. | 521/78 |
| 4,352,789 | 10/1982 | Thiel | 424/46 |

FOREIGN PATENT DOCUMENTS 0251462 5/1987 European Pat. Off. .
2029441 3/1980 United Kingdom .

OTHER PUBLICATIONS

Seifen-Ole-Fetre-Wachse, vol. 98, No. 15, 1972, pp. 489-491; W. Lanzendorf.

*Primary Examiner*—Robert L. Stoll
*Assistant Examiner*—Joseph D. Anthony
*Attorney, Agent, or Firm*—Sprung, Horn, Kramer & Woods

[57] ABSTRACT

An aerosol composition containing a composite powder and one or more of propane, isobutane, n-butane and a liquefied petroleum gas (i.e., LPG) which is a mixture thereof, a chlorinated hydrocarbon and dimethyl ether.

7 Claims, No Drawings

AEROSOL COMPOSITION

CROSS-REFERENCE TO RELATED APPLICATION

This application is a continuation-in-part of Ser. No. 07/366,836 filed Jun. 15, 1989, now abandoned.

BACKGROUND OF THE INVENTION

1. Field of the Invention

The present invention relates to an aerosol composition having a very good dispersibility and an excellent useability due to a composite powder formulated therein. The aerosol composition of the present invention can be utilized in such fields as drugs, quasi-drugs, cosmetics, sterilizers, and lubricants.

2. Description of the Related Art

Usually, a powder spray comprising a powder dispersed in a liquefied gas propellant is used as a dry shampoo, foot powder, sterilizer, lubricator, and dry type antisweat agent. The dry type antisweat agent presently used is widely sold on the market.

A chlorofluorocarbon (CFC) is widely used as the propellant for these powder sprays, due to its ease of handling.

Currently, because of the influence of this gas on the ozone layer, there is movement to restrict the use of chlorofluorocarbon, and the present trend is toward a reduction of the amount of chlorofluorocarbon used or finding a substitute therefor.

The powder spray gas generally contains, as the lubricator, talc, mica, silica, and spherical nylon, as a sweat preventive and deodorant, and powder of aluminum chloride, aluminum hydroxychloride, zinc oxide, and hydroxyapatite formulated therein.

If, however, the use of chlorofluorocarbon gases such as commercially available Freon gas as the propellant is restricted, the dispersibility of the powder is poor when these powders are formulated, and even when used after strong shaking, the powder may be sedimented during spraying, and thus it is not possible to ensure spraying for a relatively long period of a uniform composition.

SUMMARY OF THE INVENTION

Accordingly, an object of the present invention is to obviate the above-mentioned problems and to provide an aerosol composition having an excellent dispersibility and useability even if a chlorofluorocarbon gas is not used or the amount of the chlorofluorocarbon gas is restricted.

Other objects and advantages of the present invention will be apparent from the following description.

In accordance with the present invention, there is provided an aerosol composition comprising at least one propellant selected from the group consisting of propane, isobutane, n-butane, and a liquefied petroleum gas (abbreviated hereinafter as "LPG") which is a mixture thereof, a chlorinated hydrocarbon and dimethyl ether, and a composite powder.

In accordance with the present invention, there is also provided an aerosol composition comprising at least one propellant selected from the group consisting of propane, n-butane, and isobutane, at least one solvent selected from the group consisting of n-pentane, isopentane, and n-hexane, and a composite powder.

DESCRIPTION OF THE PREFERRED EMBODIMENTS

The composite powder usable in the present invention comprises one or more coating powder(s) which becomes a sheath (hereinafter abbreviated as sheath powder) attached as a composite around the powder which becomes the core (hereinafter abbreviated as the core powder). The sheath powder can be selected from among inorganic powders and organic powders as desired.

As the core powder of the composite powder usable in the present invention, any desired organic powder with a density of 0.7 to 2.0 and an average particle size of 0.1 to 100 μm can be used, and the powder used for the core can be in the form of a spheroid, plate, granule, or needle, but in view of the feeling on the skin during use of the aerosol composition, the spheroid, granular or plate form is preferred.

Typical examples of the core powder of the composite powder are polyamides such as nylon 6, nylon 12, nylon 46, and nylon 66; polyolefins such as polyethylene and polypropylene; polystyrene; polyesters such as polyethyleneterephthalate and polycarbonate; acrylic resins such as polymethyl methacrylate and butyl acrylate-MMA copolymer; epoxy resins such as cured bisphenol A-epichlorohydrin copolymer; fluorine type resins such as polytetrafluoroethylene; silicone type resins such as methylpolysiloxane and crosslinked dimethylpolysiloxane; phenolic resins such as benzoguanamine resin; vinyl resins such as polyvinyl chloride and polyvinyl methyl ether; vinylidene resins such as polyvinylidene chloride; polyurethane; cellulose; chitin; chitosan; fibroin; keratin; natural rubber; and so on.

The sheath powder, which is attached to the core powder to form the composite powder, preferably has an average particle size of 1/5 or less, more preferably 1/10 or less, of that of the core powder. If the average particle size of the sheath powder is larger than 1/5 of the average particle size of the core powder, the elimination stability of the sheath powder will be extremely poor. The preferable density of the sheath powder is 0.7 to 7.

Typical examples of the sheath powder usable in the present invention include, as inorganic powders in general, anhydrous silicic acid, magnesium silicate, talc, kaolin, bentonite, aerosil, mica, mica titanium, bismuth oxychloride, zirconium oxide, magnesium oxide, zinc oxide, titanium oxide, light calcium carbonate, heavy calcium carbonate, light magnesium carbonate, heavy magnesium carbonate, yellow iron oxide, red iron oxide, black iron oxide, ultramarine, carbon black, caramine hydroxyapatite, magnesium aluminometasilicate, magnesium aluminosilicate, aluminum hydroxychloride, aluminum chloride, aluminum sulfate, aluminum citrate, aluminum acetate, basic aluminum chloride, aluminum phenolsulfonate, aluminum β-naphtholdisulfonate, lead acetate, sodium perborate, aluminum zirconium octachlorohydrate, aluminum zirconium pentachlorohydrate, aluminum zirconium tetrachlorohydrate, aluminum zirconium trichlorohydrate, and zirconium chlorohydrate; as organic pigments, pearl pigments such as mica coated with titanium oxide, bismuth oxychloride coated with titanium oxide, bismuth oxychloride, talc coated with titanium oxide, fish scale, mica coated with colored titanium oxide; metal powder pigments such as aluminum powder and copper powder; organic pigments such as Red color No. 201, Red color No. 202, Red color No. 204, Red color No. 205, Red color No. 220, Red color No. 226, Red color No. 228, Red color No. 405, Orange color No. 203, Orange color No. 204, Yellow color No. 205, Yellow color No. 401, and Blue color No. 404; zirconium, barium or aluminum lake such as Red color No. 3, Red color No. 104, Red color No. 106, Red color No. 227, Red color No. 230, Red color No. 401, Red color No. 505, Orange color No. 205, Yellow color No. 4, Yellow color No. 5, Yellow color No. 202, Yellow color No. 203, Green color No. 3 and Blue color No. 1; as organic powders, polyamides such as nylon 6, nylon 12, and nylon 66; polyolefins such as polyethylene and polypropylene; polystyrene; polyesters such as polyethyleneterephthalate and polycarbonate; acrylic resins such as polymethyl methacrylate and butyl acrylate-MMA copolymer; epoxy resins such as cured bisphenol A-epichlorohydrin copolymer; fluorine type resins such as polytetrafluoroethylene; silicone type resins such as methylpolysiloxane and crosslinked dimethylpolysiloxane; phenolic resins such as benzoguanamine resin; vinyl resins such as polyvinyl chloride and polyvinyl methyl ether; vinylidene resins such as polyvinylidene chloride; polyurethane; cellulose; chitin; chitosan; fibroin; keratin; natural rubber; metalic soaps such as aluminum stearate, calcium stearate, magnesium stearate, zinc stearate, aluminum myristate, calcium, myristate, magnesium myristate, zinc myristate, aluminum palmitate, calcium palmitate, magnesium palmitate, zinc palmitate, zinc laurate, zinc undecylenate and calcium acetate; chlorophyll; tannin powder, and flavonoid.

As the method of preparing the composite powder to be used in the present invention, for example, the composite powder can be prepared by mixing the core powder and the sheath powder by the dry process or the wet process.

As the mixing or pulverization devices used for the manufacture of the spherical composite powder according to the present invention, a tumbling mill, vibration ball mill, satellite ball mill, sand mill, attriter and the like may be used. These mixers, however, conventionally use balls having an average size of 30 mm or more as the mixing medium, and when such a ball mill is used, the core powder and coating powder are sometimes pulverized and deformed and the frequency of contact with the powder is low, and thus it is sometimes impossible to manufacture a composite powder wherein the core powder is completely covered by the coating powder. Therefore, the ball shaped mixing medium used for the manufacture of the spherical composite powder must have an average size of 5 mm or less, and from the viewpoint of good workability, preferably 2 to 5 mm.

As mentioned above, if the average size of the ball shaped mixing medium is larger than 5 mm, the core powder cannot be substantially completely covered or a deformation or pulverization of the powder will occur, and this is not preferable. There is no particular limitation to the materials of the ball shaped mixing medium of the mixer used in the manufacture of the spherical composite powder, and ceramic, metal, or plastic materials all may be used.

There is no particular limitation of the amount of powder and the amount of mixing medium of the mixer in the manufacture of the spherical composite powder, but generally speaking, the larger the amount of mixing medium vis-a-vis the amount of powder, the greater the mixing and compressing effect, and thus the faster the processing is completed; but this in turn quickly leads to a deformation of the spherical composite powder. Further, the lower the amount of mixing medium, the smaller the compressing effect and the longer the processing, but the lower the deformation of the spherical composite powder. Therefore, preferably the amount of mixing medium used is 300 to 700 parts by weight to 100 parts of the overall powder.

In the manufacture of the above-mentioned spherical composite powder, a top open space must exist inside the mixer when the ball-shaped mixing medium is charged therein. Preferably, the top open space comprises one-third to two-thirds of the inner volume of the mixer.

The temperature of the mixer during processing is not critical, as long as it does not impair the properties and shape of the powder used.

Further, the atmosphere in the top open space of the mixture during the processing is not critical. Note that it is preferable to mix the core powder and the coating powder with a Henschel mixer or other well-known powder mixer before the mixing and compressing treatment. Further, concurrent use may be made of water, alcohol, or other liquids in the powder under treatment by the mixer in the working of the present invention.

As mentioned above, in the manufacture of the composite powder, by using the mixer with a ball shaped mixing medium having an average size of 5 mm or less, it is possible to minimize the pulverizing effect on the powder and to greatly increase the frequency of contact, and thus promote a strong bonding of the coating powder adhered to the surface of the core powder by static electricity, etc., which enables the manufacture of a composite powder with a uniform particle size, with the core powder substantially completely covered by the coating powder, and with a superior stability against separation.

In addition to the above-mentioned mixing or pulverization devices, any powder treatment apparatus such as a hybridization system, mechanofusion system and mixing devices such as an automated mortar can be conventionally used in the present invention.

The mixing ratio of the core powder to the sheath powder is preferably, in terms of weight ratio, 0.1 to 200 parts, more preferably 1 to 200 parts of the outer wall powder, per 100 parts of the core powder. At a level of less than 0.1 part, the effect of the sheath powder cannot be exhibited. When used, a powder surface modifier is incorporated in an amount of 0.01% to 10% by weight, based upon the core powder and the sheath powder.

In the practice of the present invention, the use of the composite powder having a modified surface is preferable from the viewpoint of the effects thereof. As a method of preparing the surface modified composite powder, the composite powder is prepared after the core powder and/or the sheath powder are surface modified; the composite powder is prepared by adding a surface modifier to the core powder and the sheath powder during the composite powder preparation step; and the surface modification is effected after the preparation of the composite powder and the like.

Typical examples of the surface modifier include oils such as ester oils, hydrocarbon oils, fatty acids, and silicone oils (e.g., methylhydrogen polysiloxane, 1,3,5,7-tetramethylcyclotetrasiloxane, dimethylpolysiloxane, methylphenylpolysiloxane); waxes such as whale wax, Japan wax, shellac, beeswax, lanolin, carnauba wax, and canderilla; coupling agents such as silane coupling agents (e.g., vinyl trichrolosilane, triethoxy vinylsilane, 3-chloropropyl trimethoxysilane); sillylating agents (e.g., trimethylchloro silane, hexamethyl disilazane, diethylamino trimethyl silane), titanate coupling agents (e.g., methyltrichloro titanium, isopropyltriisostearoyl titanate, tetraoctyl bis (ditridecyl phosphite) titanate, bis(dioctyl pyrophosphate)ethylene titanate); monomers forming synthetic polymers (e.g., polyamine forming monomers such as caprolactum), polyolefin forming monomers such as ethylene and propylene, styrene monomers, polyester forming monomers such as divalent aromatic phenols and bis phenol A, acryl resin forming monomers such as methyl methacrylate, methacrylic acid, butyl methacrylate, epoxy resin monomers such as bisphenol A and epichlorohydrin, fluorine resin monomers, silicone resin monomers; surfactants such as alkylallyl sulfonates, sulfuric acid ester salts of higher alcohols, phosphoric acid ester salts of higher alcohols; silicone surfactants such as polyether modified silicone, amino modified silicone, alkyl modified silicone, alcohol modified silicone, and carboxylic acid modified silicone; fluorine surfactants such as perfluoroalkyl carboxylic acid salts, perfluoroalkyl phosphoric acid esters, perfluoroalkyl carboxylic acid salts, perfluoroalkyl trimethylammonium salts, perfluoroalkyl betains, perfluoroalkylamine oxides, and perfluoroalkyl ethylene oxide addition products; metal soaps such as aluminum stearate, calcium stearate, magnesium stearate, zinc stearate, aluminum myristate, calcium myristate, magnesium myristate, zinc myristate, aluminum palmitate, calcium palmitate, magnesium palmitate, zinc palmitate, zinc laurate, zinc undecylate, and calcium acetate; silicone resins; silicone rubber; gelatin; collagen; keratin; and fibroin.

As the surface modification method, any connectional modification methods may be used in the present invention. Examples of such methods are modification by coating, topochemical modification, mechanochemical modification, modification by encapsulation, radiation modification, and plasma irradiation modification. These methods are carried out under, for example, the vapor phase, the liquid phase or in vacuo. Furthermore, the composite powder may be modified only by, for example, plasma irradiation, without using the surface modifier.

The amount of the composite powder formulated in the present invention is preferably 0.1% to 30% by weight in the total amount of the aerosol composition, more preferably 0.3% to 20% by weight. If the amount is less than 0.1%, the effect required from the powder formulation cannot be obtained, and the effect will be unchanged if the amount formulated is more than 30% by weight.

The propellant usable in the present invention is one or more of propane, isobutane, n-butane, and LPG, which is a mixture thereof, chlorinated hydrocarbons such as methyl chloride and methylene chloride and dimethyl ether, and these propellants can be further used in combination with chlorofluorocarbon gases such as Freon 11, Freon 12, Freon 21, Freon 113, and Freon 114 (all trademarks marketed from E. I. Dupont).

When chlorofluorocarbon gases are used in combination, if the average specific gravity is 1.2 or less, the required dispersibility effect is obtained. Accordingly, when the specific gravity of the propellant becomes 1.2 or less, if the powder formulated in the powder spray of the prior art is now formulated, although the dispersibility is worsened it can be improved by a formulation of the composite powder of the present invention. Also, to control the inner pressure and dissolve the formulated product, a solvent as represented by an alcohol also can be formulated in the composition. Examples of such solvents are alcohol, n-pentane, isopentane, n-hexane, cyclohexane, isohexane, n-heptane, isooctane, 2,2-dimethylbutane, petroleum ether, petroleum benzene, ligroin, 2-pentene, methyl ethyl ether, and diethyl ether. Typically, inner pressure is 0.1 to 3.0 kg/cm$^2$ G (gauge) at a temperature of 20° C.

The amount of propellant formulated is preferably 5 to 99% by weight of the total amount of the aerosol composition, more preferably 15 to 95% by weight. A good jetting state cannot be obtained at a level of less than 5% by weight.

In the composition of the present invention, in addition to the above components, any of the optional components known in the art can be formulated.

Examples of such formulation components include water; oils and fats such as avocado oil, almond oil, olive oil, grapeseed oil, sesame oil, Sasanqua oil, safflower oil, soybean oil, Tsubaki (camellia) oil, corn oil, rapeseed oil, persic oil, castor oil, sunflower oil, cottonseed oil, peanut oil, cacao oil, palm oil, coconut oil, tallow, fish fat, hardened oil, turtle oil, lard, mink oil, and egg yolk oil; waxes such as whale wax, shellac, beeswax, lanolin, liquid lanolin, carnauba wax, and canderilla wax; hydrocarbons such as liquid paraffin, liquid polyisobutylene, squalane, pristane, petrolatum, paraffin, and ceresin; silicone oils such as dimethyl polysiloxane, methyl phenyl polysiloxane, methylhydrogen polysiloxane, octamethyl cyclo tetrasiloxane, and decamethyl cyclopentasiloxane; fatty acids such as succinic acid, tartaric acid, citric acid, undecyleic acid, lauric acid, myristic acid, palmitic acid, stearic acid, isostearic acid, oleic acid, linoleic acid, ricinoleic acid, and behenic acid; alcohols such as ethanol, isopropanol, lauryl alcohol, cetanol, 2-hexyldecanol, stearyl alcohol, isostearyl alcohol, oleyl alcohol, and lanolin alcohol; polyhydric alcohols such as ethylene glycol, diethylene glycol monoethyl ether, triethylene glycol, polyethylene glycol, propylene glycol, 1,3-butylene glycol, glycerine, and butyl alcohol; sugars such as glucose, sucrose, lactose, xylitol, sorbitol, mannitol, and maltitol; esters such as diisopropyl adipate, hexyldecyl isostearate, cetyl isooctanoate, olecyl oleate, decyl oleate, lanolin acetate, butyl stearate, isopropyl myristate, diethyl phthalate, and hexyl laurate; metal soaps such as aluminum stearate, magnesium stearate, zinc stearate, aluminum myristate, calcium myristate, magnesium myristate, zinc myristate, aluminum palmitate, calcium palmitate, magnesium palmitate, zinc palmitate, zinc laurate, zinc undecylate, and calcium acetate; natural water soluble polymeric compounds such as gum arabic, sodium alginate, casein, carageehnan, karaya gum, agar, quinceseed, gelatin, dextrin, starch, tragacanth, and pectin; natural dyes such as chlorophil and $\beta$-carotin; sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; glycerol polyglycerol fatty acids such as mono cottonseed oil fatty acid glycerol, monoerucic acid glycerol, sesquioleic acid glycerol, monostearic acid glycerol, $\alpha,\alpha'$-oleic acid pyroglutamic acid glycerol, monostearic acid glycerol malic acid; propylene glycol fatty acid esters such as propylene glycerol monostearate; lipophilic nonionic surfactants such as hydrogenated castor oil derivatives, glycerol alkylethers; polyoxyethylene (i.e., POE) fatty acid esters such as POE sorbitan monooleate, POE sorbitan monostearate, POE sorbitan monooleate, POE sorbitan pentaoleate, and POE sorbitan tetraoleate; POE sorbitol fatty acid esters such as POE sorbitol monolaurate, POE sorbitol monooleate, POE sorbitol pentaoleate, POE sorbitol monostearate; POE glycerol fatty acid esters such as POE glycerol monostearate, POE glycerol monoisostearate, and POE glycerol triisostearate; POE fatty acid esters such as POE monooleate, POE distearate, POE monodioleate and ethylene glycol distearate; POE alkylethers such as POE lauryl ether, POE oleyl ether, POE stearyl ether, POE behenyl ether, POE 2-octyldodecyl ether, POE cholestanol ether; POE alkyl phenyl ethers such as POE octyl phenyl ether, POE nonyl phenyl ether, and POE dinonyl phenyl ether; Pluronic type surfactants such as Pluronic; POE.POP alkyl ethers such as POE.POP cetyl ether, POE.POP 2-decyl tetradecyl ether, POE. POP monobutyl ether, POE.POP hydrogenated lanolin, and POE.POP glycerol ether; tetra POE.tera POP ethylenediamine condensates such as Tetronic; POE castor oil hydrogenated castor oil derivatives such as POE castor oil, POE hydrogenated castor oil, POE hydrogenated castor oil monoisostearate, POE hydrogenated castor oil-isostearate, POE hydrogenated castor oil monopyroglutamic acid monoisostearic acid diester, and POE hydrogenated castor oil maleic acid; POE beeswax.lanolin derivatives such as POE sorbitol beeswax; alkanol amides such as coconut oil fatty acid diethanolamide, lauric acid monoethanol amide; hydrophilic nonionic surfactants such as POE propylene glycol fatty acid esters, POE alkylamines, POE fatty acid amides, sucrose fatty acid esters, POE nonylphenyl formaldehyde condensates, alkylethoxydimethyl amine oxides, and trioleyl phosphoric acid; fatty acid soaps such as soap bases, sodium laurate and sodium palmitate; higher alkyl sulfuric acid ester salts such as sodium lauryl sulfate, potassium lauryl sulfate; alkyl ether sulfuric acid ester salts such as POE lauryl sulfate triethanolamine and sodium POE lauryl sulfate; N-acyl sarcosinic acids such as sodium lauroyl sarcosinate; higher fatty acid amide sulfonic acid salts such as sodium N-myristoyl-N-methyl taurine, sodium coconut oil fatty acid methyltauride, and sodium lauryl methyltauride; phosphoric acid ester salts such as sodium POE oleyl ether phosphate and sodium POE stearyl ether phosphate; sulfosuccinic acid salts such as sodium di-2-ethylhexyl sulfosuccinate, sodium monolauroyl monoethanolamide polyoxyethylene sulfosuccinate, and sodium lauryl polypropyleneglycol sulfosuccinate; alkylbenzene sulfonic acid esters of, for example, linear dodecylbenzene sulfonic acid such as sodium linear dodecylbenzene sulfonate and triethanolamine linear dodecylbenzene sulfonate; N-acylglutamic acid salts such as monosodium N-lauroyl glutamic acid, disodium N-stearoyl glutamic acid, and monosodium N-myristoyl-L-glutamate; higher fatty acid ester sulfuric acid ester salts such as sodium hydrogenated coconut oil fatty acid glycerol sulfate; sulfated oil such as Turkey red oil; anionic surfactants such as POE alkyl ether carboxylic acids, POE alkyl allyl ether carboxylic acid salts, α-olefin sulfonic acid salts, higher fatty acid ester sulfonic acid salts, secondary alcohol sulfuric ester salts, higher fatty acid alkylolamide sulfuric acid ester salts, sodium lauroyl monoethanolamide succinate, N-palmytoyl aspartic acid ditriethanolamine, and sodium casein; silicone surfactants such as polyether modified silicone, amino modified silicone, alkyl modified silicone, alcohol modified silicone, and carboxylic acid modified silicone; fluorine containing surfactants such as perfluoroalkyl carboxylic acid salts, perfluoroalkyl phosphoric acid esters, perfluoroalkyl carboxylic acid salts, perfluoroalkyl trimethyl ammonium salts, perfluoroalkyl betains, perfluoroalkylamine oxide, and perfluoroalkyl EO addition products; preservatives such as butyl p-oxybenzoate, propyl p-oxybenzoate, and methyl p-oxybenzoate; vitamins such as vitamin A, vitamin D, vitamin E, and vitamin K; hormones such as estradiol, ethynylestradiol, and cortisone; antisweat agents such as aluminum hydroxychloride, aluminum chloride, aluminum sulfate, basic aluminum bromide, aluminum phenolsulfonic acid, tannic acid, aluminum naphthalenesulfonic acid, and basic aluminum iodide; UV-absorbers such as urocanic acid and cynoxate; antiphlogistics such as allantoin, aloe powder, and guaizulene; sterilizers such as 3,4,4-trichlorocarbanilide (T.C.C.), triethylcitrate (T.E.C.), benzalkonium chloride, benzotonium chloride, alkyltrimethylammonium chloride, resorcin, phenol, sorbic acid, salicylic acid, and hexachlorophen; essential oils which are natural plant perfumes such as lavender, lemon, jasmin, mint, peppermint, rose, and camphor; animal perfumes such as musk, civet, and castoreum, and other synthetic perfumes; and a compressed gas such as carbon dioxide gas, nitrogen gas, and nitrous oxide gas.

The present invention provides an aerosol composition having an excellent powder dispersibility and useability, by reducing the amount of chlorofluorocarbon gas or without using chlorofluorocarbon gas, and thus meets current requirements to restrict the use of this gas due to the influence thereof on the ozone layer.

EXAMPLE

The present invention will now be further illustrated by, but is by no means limited to, the following Examples, wherein all parts and percentages are expressed on a weight basis unless otherwise noted.

Evaluation test methods used hereinbelow will be described.

PRODUCTION OF COMPOSITE POWDER

Production Example 1

Production of Composite Powder [Spherical Nylon 12 (5 μm):Zinc Oxide (0.3 μml)=70:30]

First, 70.0% of spherical nylon 12 (average particle size 5 μm) was mixed with 30.0% of zinc oxide (average particle size 0.3 μm) in a Henschel type mixer (FM10B model, Mitsui Miike Seisakusho) for 3 minutes, and then the mixed powder was treated in a rotatory system ball mill (Yamato Kagaku, Universal Ball Mill, 5 liter pot volume, 40 rpm) filled with alumina balls (Nippon Kagaku Togyo, HD Alumina Ball 3 mmφ, 5 kg) for 10 hours.

Observation by a scanning electron microscope (scanning electron microscope, S-510 model, produced by Hitachi) confirmed that the composite powder having the particulate structure was obtained.

Production Example 2: Composite powder [spherical poly MMA (10 μm):silica (0.1 μm)=61:391]

First, 61.0% of spherical poly MMA (average particle size 10 μm) was mixed with 39.0% of silica (average particle size 0.1 μm) in a small scale pulverizer (Kyoritsu Riko, SK-M10 model) for 1 minute, and then 50 g of the mixed powder was placed in a planetary ball mill (Centrifugal Ball Mill, manufactured by Mitamura Riken Kogyo, 250 ml pot volume and dial 50) filled with alumina balls (Nippon Kagaku Togyo, HD Alumina Ball 2 mmφ), and the treatment was carried out for 1 hour. It was confirmed by scanning electron microscope observation that, in the composite powder, the surface of the spherical poly MMA was completely covered with silica.

Production Example 3: Composite powder [spherical] methyl polysiloxane (9 μm) : magnesium aluminometasilicate (0.4 μm): polymethylmethacrylate (0.7 μm) =75:20:5]

First, 75.0% of spherical methyl polysiloxane (average particle size 9 μm) was treated with 20.0% of magnesium aluminometasilicate (average particle size 0.4 μm) and 5.0% of polymethylmethacrylate (average particle size 0.7 μm) (the total weight was 3 kg) in a rotatory system ball mill (Universal Ball Mill, 25 liter pot volume, 28 rpm, manufactured by Yamato Kagaku) filled with alumina balls (HD Alumina Ball 3 mmφ, 4 kg, manufactured by Nippon Kagaku Togyo), for 8 hours to obtain a composite powder.

Production Example 4: Composite powder [plate-shaped polyethylene (8 μm): magnesium oxide (0.05 μm)= 60:40]

First, 60.0% of plate-shaped polyethylene powder (average particle size 8 μm) was placed with 39.0% of magnesium oxide (average particle size 0.05 μm) (total weight=60 g) in a planetary ball mill (Mitamura Riken Kogyo, CENTRIFUGAL BALL MILL 250 ml pot volume, dial 60) filled with alumina balls (Ashizawa Alumina Ball 1 mmφ), and the treatment was carried out for 30 minutes to obtain a composite powder.

Production Example 5: Composite powder [spherical nylon 6 (7 μm):chlorohydroxy aluminum (0.8 μm)=70:30)

First, 70.0% of spherical nylon 6 (average particle size 7.0 μm) was placed with 30.0% of chlorohydroxy aluminum (average particle size 0.8 μm) (total weight: 500 g) in a vibration system ball mill (Nippon Spindle, VKM-2 model, dial 5) filled with alumina balls (Ashizawa Alumina Ball 2 mmφ, 2 kg), and the treatment was carried out for 3 hours to obtain a composite powder.

Production Example 6: Composite powder [granular cellulose (20 μm):talc (2 μm)=74:26]

First, 74.0% of granular cellulose (average particle size 20 μm) and 26.0% of talc (average particle size 2.0 μm) (total weight=100 g) were subjected to the OM Dizer treatment for 1 minute and the hybridizer treatment (3000 rpm) for 2 minutes, using a hybridization system (NHS-O model manufactured by Nara Kikai), to obtain a composite powder.

Production Example 7: Composite cowder (spherical polystyrene (50 μm):hydroxyapatite (0.3 μm) =81:191]

First, 81.0% of spherical polystyrene (average particle size 50 μm) and 19.0% of hydroxyapatite (average particle size 0.3 μm) were thrown into the rotatory casing section of a mechanofusion system (AM-15F model manufactured by Hosokawa Micron), and the treatment was carried out at 2800 rpm for 30 minutes to obtain a composite powder.

Production Example 8: Composite powder (high viscosity silicone coated plate-shaped polyethylene (6 μm):hexamethyldisilazane treated zinc oxide (0.2 μm)=79:21]

The composite powder was obtained in the same manner as in Production Example 4 by using 79.0% of high viscosity silicone coated plate-shaped polyethylene (average particle size: 6 μm) and 21.0% of hexamethylenedisilazane treated zinc oxide (average particle size: 0.2 μm).

Production Example 9: Composite powder [spherical chitosan (20 μm):magnesium oxide (0.6 μm):zinc myristinate (0.8 μm)=79:20.5:0.5]

The composite powder was obtained in the same manner as in Production Example 7 by using 79.0% of spherical chitosan (average particle size: 20 μm), 20.5% of magnesium oxide (average particle size: 0.6 μm), and 0.5% of zinc myristinate (average particle size: 0.8 μm).

Powder Dispersibility Test

Powder and a propellant were filled in an aerosol glass bottle, and after shaking, the time in which the powder sedimented at the bottom of the bottle was measured.

Useability Test

Each sample was sprayed on the forearm for 3 seconds, and the extendability of the powder was evaluated. The evaluation standards are as follows.
++... very well extended and free flowing
+... slightly extended and free flowing
±... not well extended
−... very poorly extended

EXAMPLES 1–4 AND COMPARATIVE EXAMPLES 1–10

Tables 1 and 2 show results of Examples and Comparative Examples.

TABLE 1

| Starting material | Example 1 | Comparative Example 1 | Comparative Example 2 | Example 2 | Comparative Example 3 | Comparative Example 4 |
|---|---|---|---|---|---|---|
| Composite powder [spherical nylon 12 (5 μm):silica (0.1 μm) = 70:30 (see Production Example 1) | 2 | — | — | 2 | — | — |
| Mixed powder [spherical nylon 12 (5 μm):silica (0.1 μm) = 70:30] | — | 2 | — | — | 2 | — |
| Silica (0.1 μm) | — | — | 0.6 | — | — | 0.6 |
| LPG (isobutane) | 98 | 98 | 99.4 | — | — | — |
| LPG (isobutane)/Freon 11, 12 (50/50) = 50/50 | — | — | — | 98 | 98 | 99.4 |
| Time until sedimentation occurred after shaking (sec.) | 30 sec. | 15 sec.* | 7 sec. | 34 sec. | 18 sec.* | 10 sec. |
| Useability | ++ | ± | — | ++ | ± | — |

*only silica sedimented
specific gravity of propellant liquid (20° C.)
LPG (isobutane) 0.36
LPG/Freon (50/50) 0.98

TABLE 2

| Starting Material | Example 3 | Example 4 | Comparative Example 5 | Comparative Example 6 | Comparative Example 7 | Comparative Example 8 | Comparative Example 9 | Comparative Example 10 |
|---|---|---|---|---|---|---|---|---|
| Composite powder [spherical poly MMA (10 μm):zinc oxide (0.3 μm) = 61:39]*1 | 1.5 | 1.5 | — | — | — | — | — | — |
| Mixed powder (spherical poly MMA (10 μm):zinc oxide (0.3 μm) = 61:39] | — | — | 1.5 | — | — | 1.5 | — | — |
| Composite treated powder [spherical poly MMA (0.7 μm):zinc oxide (0.3 μm) = 61:39]*2 | — | — | — | 1.5 | — | — | 1.5 | — |
| Zinc oxide (0.3 μm) | — | — | — | — | 0.59 | — | — | 0.59 |
| LPG [(n-butane (75%)/isobutane (25%)]/ isopentane = 60/20 | 98.5 | — | 98.5 | 98.5 | 99.41 | — | — | — |
| LPG [(n-butane (75%)/isobutane (25%)/ isopentane/Freon 11/12 (50/50)] = 37.5/12.5/50 | — | 98.5 | — | — | — | 98.5 | 98.5 | 99.41 |
| Time until sedimentation occurred after shaking (sec) | 40 | 52 | 16*3 | 18*3 | 5 | 18*3 | 19*3 | 8 |
| Useability | ++ | ++ | ± | ± | — | ± | ± | — |

*1Composite powder obtained in Production Example 2
*2Composite treatment was effected in the same manner as in Production Example 2, but the desired composite powder was not obtained because of the small particle size of spherical poly MMA
*3Only zinc oxide sedimented
Note:
Specific gravity of propellant liquid (20° C.) LPG (n-butane (75%)/isobutane (25%): 0.574, Isopentane: 0.620, CFC (Freon 11/12 (50/50)): 1.39

*1: Composite powder obtained in Production Example 2

*2: Composite treatment was effected in the same manner as in Production Example 2, but the desired composite powder was not obtained because of the small particle size of spherical poly MMA

*3 Only zinc oxide sedimented

Note: Specific gravity of propellant liquid (20° C.) LPG (n-butane (75%)/isobutane (25%): 0.574, Isopentane: 0.620, CFC (Freon 11/12 (50/50)): 1.39

As shown in Tables 1 and 2, in Examples 1-4, the time taken for the powder to precipitate after shaking was remarkably lengthened. In the case of the propellant liquid with a specific gravity of 1.2 or less, those formulated with the composite powder had an extremely good dispersibility, with the sedimentation time being prolonged 3-fold to 4-fold compared to the silica formulated product of the Comparative Examples. Also, the useability of the present Examples was found to be significantly better, compared with Comparative Examples formulated with conventional silica.

EXAMPLE 5: DEODORANT SPRAY

| | |
|---|---|
| (1) Composite powder [spherical methylpolysilocane (9 μm):magnesium metalsilicate aluminate (0.4 μm): polymethyl methacrylate (0.7 μm) = 75:20:5] (see Production Example 3) | 5.0 |
| (2) Isopropyl myristate | 0.6 |
| (3) Alcohol | 10.0 |
| (4) Aluminum hydroxychloride | 0.2 |
| (5) Perfume | 0.2 |
| (6) L.P.G. (isobutane) | 50.0 |
| (7) Freon 12 | 14.0 |
| (8) Freon 114 | 20.0 |
| Average specific gravity of propellant | 0.905 |

After the components (1) to (5) were filled in an aerosol can, a valve was mounted and crimped, and the components (6) to (8) were filled under pressure to obtain a deodorant spray. The spray had a good powder dispersibility and useability.

EXAMPLE 6: COLOGNE POWDER SPRAY

| | |
|---|---|
| (1) Composite powder [plate polyethylene (8 μm):magnesium oxide (0.05 μm) = 60:40] (see Production Example 4) | 15.0 |
| (2) Perfume | 3.0 |
| (3) Polymethylsiloxane | 1.0 |
| (4) L.P.G. [propane (10%)/n-butane (90%)] | 51.0 |
| (5) Dimethyl ether | 30.0 |
| Average specific gravity of propellant | 0.605 |

After (1) to (3) were filled in an aerosol can, a valve was mounted and crimped, and the components (4) and (5) were filled under pressure to obtain a cologne powder spray. The spray was found to have a good powder dispersibility and useability.

EXAMPLE 7: DEODORANT SPRAY

| | |
|---|---|
| (1) Composite powder [spherical nylon 6 (7 μm):chlorohydroxy aluminum (0.8 μm) = 70:30] (see Production Example 5) | 10.0 |
| (2) Benzotonium chloride | 0.05 |
| (3) Alcohol | 20.0 |
| (4) Spherical silica | 0.5 |
| (5) Deionized water | 5.0 |
| (6) Dimethyl ether | 34.45 |
| (7) L.P.G. (isobutane) | 30.0 |
| Average specific gravity of propellant | 0.613 |

After the components (1) to (5) were filled in an aerosol can, a valve was mounted and crimped, and the components (6) and (7) were filled under pressure to obtain a deodorant spray. The spray was found to have a good powder dispersibility and useability.

EXAMPLE 8: POWDER COLOGNE SPRAY

| | |
|---|---|
| (1) Composite powder [particulate cellulose (20 μm):talc (2 μm) = 74:26] (see Production Example 6) | 3.0 |
| (2) Dipropylene glycol | 1.0 |
| (3) Ethyl alcohol | 53.6 |
| (4) Water | 12.0 |
| (5) Camphor | 0.2 |
| (5) Perfume | 0.2 |
| (7) Dimethyl ether | 30.0 |
| Average specific gravity of propellant | 0.66 |

After the components (1) to (6) were homogeneously mixed, the mixture was filled in an aerosol can and a valve was mounted and crimped. After crimping, (7) was filled under pressure to obtain a powder cologne spray. The spray was found to have a good powder dispersibility and useability.

EXAMPLE 9: DEODORANT POWDER SPRAY

| | |
|---|---|
| (1) Composite powder [spherical polystyrene (50 μm):hydroxyapatite (0.3 μm) = 81:19] (see Production Example 7) | 7.0 |
| (2) Ethyl alcohol | 39.8 |
| (3) Water | 10.0 |
| (4) Propylene glycol | 3.0 |
| (5) Aluminum hydroxychloride (50%) | 10.0 |
| (6) Perfume | 0.2 |
| (7) Dimethyl ether | 25.0 |
| (8) L.P.G. (butane) | 5.0 |
| Average specific gravity of propellant | 0.65 |

The components (1) to (6) were homogeneously mixed and then filled in an aerosol can, and a valve was mounted and crimped, followed by filling (7) and (8) to obtain a deodorant powder spray. The spray was found to have a good powder dispersibility and useability.

EXAMPLE 10: POWDER SPRAY

| | |
|---|---|
| (1) Composite powder [granular tetrafluoroethylene (1 μm):kaolin (0.1 μm) = 91:9] | 4.7 |
| (2) Ethyl alcohol | 27.0 |
| (3) Water | 9.0 |
| (4) Potassium glycyrrhizinate | 0.1 |
| (5) Perfume | 0.2 |
| (6) Freon 11/12 (80/20) | 36.0 |
| (7) Dimethyl ether | 18.0 |
| Average specific gravity of propellant | 1.19 |

After the components (1) to (5) were mixed, the mixture was filled in an aerosol can, and a valve was mounted and crimped, followed by filing (6) and (7) under pressure to obtain a powder spray. The spray was found to have a good powder dispersibility and useability.

EXAMPLE 11: POWDER SPRAY FOR SYSTEMIC USE

| | |
|---|---|
| (1) Composite powder [granular chitosan (30 μm):magnesium silicate aluminate (0.5 μm) = 69:31] | 10.0 |
| (2) Mentol | 0.1 |
| (3) Camphor | 0.2 |
| (4) Eucalyptus oil | 0.1 |
| (5) Ethanol | 39.6 |
| (6) Freon 12 | 10.0 |
| (7) Dimethyl ether | 40.0 |
| Average specific gravity of propellant | 0.794 |

A solution of (2) to (4) dissolved in the components (1) and (5) was filled in an aerosol can and a valve was mounted and crimped, followed by filling (6) and (7) under pressure to obtain a powder spray for systemic use. The spray was found to have a good powder dispersibility and useability.

EXAMPLE 12: DEODORANT COLOGNE SPRAY

| | |
|---|---|
| (1) Composite powder [particulate fibroin (25 μm):particulate chitin (2 μm): light calcium carbonate (1 μm) = 69:19:12 | 5.0 |
| (2) Trichlosane | 0.1 |
| (3) Ethanol | 30.0 |
| (4) Aluminum hydroxychloride (50%) | 10.0 |
| (5) Water | 10.0 |
| (6) Perfume | 0.1 |
| (7) Polyoxyethylene (60 mole adduct) hydrogenated castor oil derivative | 0.5 |
| (7) Dimethyl ether | 40.0 |
| (8) L.P.G. (butane) | 4.3 |
| Average specific gravity of propellant | 0.652 |

After (2), (6) and (7) were dissolved in the components (1) and (3), (4) and (5) were added, and the mixture filled in an aerosol can. A valve was mounted and crimped, followed by filling (8) and (9) under pressure to obtain a deodorant cologne spray. The spray was found to have a good powder dispersibility and useability.

EXAMPLE 13: DEODORANT POWDER SPRAY

| | |
|---|---|
| (1) Composite powder [spherical polymethyl methacrylate (0.5 μm):aluminum hydroxychloride (0.05 μm)] = 60:40 | 15.0 |
| (2) Talc | 1.0 |
| (3) Isopropyl myristate | 0.5 |
| (4) Tetra-2-ethylhexanoic acid diglycerolsorbitane | 0.5 |
| (5) Dimethyl ether | 30.3 |
| (6) L.P.G. | 50.0 |
| Average specific gravity of propellant | 0.677 |

After the components (1) to (4) were homogeneously mixed, the mixture was filled in an aerosol can. A valve was mounted and crimped, followed by filling (5) and (6) under pressure to obtain a deodorant powder spray. The spray was found to have a good powder dispersibility and useability.

EXAMPLE 14: DEODORANT SPRAY

| | |
|---|---|
| (1) Composite powder [spherical crosslinked polymethyl methacrylate (15 μm): aluminum hydroxy chloride (0.5 μm): silicone resin = 70:26:4] | 7.0 |
| (2) Isopropyl myristate | 0.7 |
| (3) Ethanol | 8.0 |
| (4) Perfume | 0.1 |
| (5) L.P.G. [n-butane (75%)/isobutane (25%)] | 84.2 |
| Average specific gravity of propellant | 0.588 |

After the components (1) to (4) were uniformly mixed and filled in an aerosol can, a valve was mounted and crimped, and the component (5) was filled under pressure to obtain a deodorant spray.

EXAMPLE 15: COLOGNE POWDER SPRAY

| | |
|---|---|
| (1) Composite powder [granular nylon 46 (7 μm):basic aluminum (0.2 μm): squalane:carnauba wax] = 80:25:2.5:2.5] | 13.0 |
| (2) Perfume | 3.0 |
| (3) Polymethylphenylsiloxane | 2.0 |
| (4) L.P.G. [n-butane (90%)/propane (10%)] | 50.0 |
| (5) Dimethyl ether | 30.0 |
| Average specific gravity of propellant | 0.572 |

After (1) to (3) were filled in an aerosol can, a valve was mounted and crimped, and the components (4) and (5) were filled under pressure to obtain a cologne powder spray.

EXAMPLE 16: FOOT SPRAY

| | |
|---|---|
| (1) Composite powder [granular crosslinked polystyrene (12 μm):aluminum citrate (0.4 μm):calcium stearate (0.7 μm) = 64:35.2:0.8] | 10.0 |
| (2) Composite powder [spherical benzoguanamine resin (10 μm):zinc oxide (0.04 μm) - 75:25] | 10.0 |
| (3) Dimethyl polysiloxane | 5.0 |
| (4) Perfume | 0.9 |
| (5) L.P.G. [Propane (43.0%/isobutane (16%)/n-butane (41%)] | 44.5 |
| (6) n-pentane | 29.6 |
| Average specific gravity of propellant | 0.543 |

After (1) to (4) were uniformly mixed and filled in an aerosol can, a valve was mounted and crimped, and the component (5) was filled under pressure to obtain a foot spray.

The powder dispersibility and useability of the products obtained in Examples 14, 15, and 16 were evaluated as mentioned above. The results are shown in Table 3.

TABLE 3

| | Example | | |
|---|---|---|---|
| | 14 | 15 | 16 |
| Time until sedimentation occurred after shaking (sec) | 123 | 84 | 98 |
| Useability | ++ | ++ | ++ |

As is clear from the results shown in Table 3, the products of Examples 14 to 16 had an excellent dispersibility and useability.

EXAMPLE 17: DEODORANT SPRAY

| | |
|---|---|
| (1) Composite powder [flakypolyethylene coated with high viscosity silicone (6 μm):hexamethyldisilazane treated zinc oxide (0.2 μm) = 79:21 (see Production Example 8) | 11.0 |
| (2) Ethanol | 38.0 |
| (3) Water | 9.0 |
| (4) Propylene glycol | 3.0 |
| (5) Perfume | 0.3 |
| (6) L.P.G [n-butane (52.5%)/isobutane (17.5%)/propane (30.0%)] | 38.7 |
| Average specific gravity of propellant | 0.553 |

After the component (1) to (5) were uniformly mixed and filled in an aerosol can, a valve was mounted and crimped, and the component (6) was filled under pressure to obtain a deodorant spray. The spray obtained was found to have a good powder dispersibility, useability, and deodorizing property.

EXAMPLE 18: POWDER SPRAY

| | |
|---|---|
| (1) Composite powder [spherical cured bisphenol A-epichlohydrin copolymer powder (18 μm):mica coated with high viscosity methylphenyl polysiloxane (0.9 μm) = 61:39)] | 14.0 |
| (2) Talc | 1.2 |
| (3) Isopropyl myristate | 0.8 |
| (4) L.P.G. [n-butane (45%)/isobutane (15%)/propane (40%) | 84.0 |
| Average specific gravity of propellant | 0.545 |

Ater the components (1) to (3) were uniformly mixed and filled in an aerosol can, a valve was mounted and crimped. After crimping, the component (4) was filled under pressure to obtain a powder spray. The spray was found to have a good powder dispersibility and useability.

EXAMPLE 19: POWDER SPRAY FOR SYSTEMIC USE

| | |
|---|---|
| (1) Composite powder [granular polypropylene (18 μm):zinc oxide (0.05 μm):silicone resin = 71:28:1] | 11.0 |
| (2) Mentol | 0.2 |
| (3) Camphor | 0.1 |
| (4) Eucalyptus oil | 0.1 |
| (5) Ethanol | 38.6 |
| (6) L.P.G. [n-butane (49%)/isobutane (16%)/propane (35%)] | 37.5 |
| (7) Freon 11 | 12.5 |

-continued

| | |
|---|---|
| Average specific gravity of propellant | 0.776 |

After the components (1) to (5) were mixed, the mixture was filled in an aerosol can, and a valve was mounted and crimped, followed by filling (6) and (7) under pressure to obtain a powder spray. The spray was found to have a good powder dispersibility and useability.

EXAMPLE 20: POWDER SPRAY

| | | |
|---|---|---|
| (1) | Composite powder [spherical chitosan (20 μm):magnesium oxide (0.6 μm):zinc myristate (0.8 μm) = 79:20.5:0.5] (see Production Example 9) | 13.5 |
| (2) | Spherical silica | 0.5 |
| (3) | Squalane | 2.5 |
| (4) | Methylphenyl polysiloxane | 2.0 |
| (5) | Isopentane | 16.3 |
| (6) | L.P.G. [n-butane (75%)/isobutane (25%)] | 65.2 |
| Vapor pressure of a mixture of (5) and (6): | | 1.1 kg/cm²G (gauge) at 20° C. |

The components (1) and (2) and the components (3) and (4) were separately uniformly mixed. The resultant mixtures and the component (5) were then filled in an aerosol can, and a valve was mounted and crimped, followed by filling the component (6) under pressure to obtain a powder spray.

EXAMPLE 21: FOOT SPRAY

| | | |
|---|---|---|
| (1) | Composite powder [granular polyvinylidene chloride (7 μm):calcium oxide treated with perfluoroalkyl-phosphoric acid ester (0.9 μm) = 61:39] | 13.0 |
| (2) | Aluminum stearate | 0.4 |
| (3) | Aluminum hydroxy chloride | 1.0 |
| (4) | Octamethyl cyclotetrasiloxane | 2.5 |
| (5) | Decamethyl cyclopentasiloxane | 2.5 |
| (6) | n-pentane | 48.36 |
| (7) | LPG [propane (43%)/isobutane (16%)/n-butane (41%)] | 32.24 |
| Vapor pressure of a mixture of (6) and (7): | | 1.4 kg/cm²G (20° C.) |

The components (1) to (3) and the components (4) and (5) were separately uniformly mixed and then filled, together with the component (6), in an aerosol can, and a valve was mounted and crimped, followed by filling the component (7) under pressure to obtain a foot spray.

We claim:

1. An aerosol composition comprising about 0.1 to 30% by weight of an undissolved composite powder and about 5 to 99% by weight of at least one propellant selected from the group consisting of propane, n-butane, isobutane, a liquefied petroleum gas, a chlorinated hydrocarbon and dimethyl ether, said composite powder comprising a core powder and a sheath powder attached to the surface of the core powder, said core powder having a density of 0.7 to 2.0 g/cm³ and an average particle size of 0.1 to 100 μm and consisting essentially of a polymer, and said sheath powder having an average particle size at most 1/5 that of the core powder.

2. An aerosol composition as claimed in claim 1, further comprising a chlorofluorocarbon gas.

3. An aerosol composition comprising about 5 to 99% by weight of at least one propellant selected from the group consisting of propane, n-butane, isobutane and a liquefied petroleum gas, at least one solvent selected from the group consisting of n-pentene, isopentane and n-hexane, and aobut 0.1 to 30% by weight of an undissovled composite powder, said composite powder comprising a core powder and a sheath powder attached to the surface of the core powder, said core powder having a density of 0.7 to 2.0 g/cm³ and an average particle size of 0.1 to 100 μm and consisting essentially of a polymer, and said sheath powder having an average particle size at most 1/5 that of the core powder.

4. An aerosol composition as claimed in claim 3, wherein the vapor pressure of a mixture of the propellant and the solvent is 0.1 to 3.0 kg/cm²G at 20° C.

5. An aerosol composition as claimed in claim 3, further comprising a chlorofluorocarbon gas.

6. An aerosol composition as claimed in claim 1, wherein said core powder consists essentially of at least one polymer selected from the group consisting of polyamides, polyolefins, polystyrene, polyesters, acrylic resins, epoxy resins, fluorine type resins, silicone type resins, phenolic resins, vinyl resins, polyurethane, cellulose, chitin, chitosan, fibroin, keratin and natural rubbers.

7. An aerosol composition as claimed in claim 3, wherein said core powder consists essentially of at least one polymer selected from the group consisting of plyamides, polyolefins, polystyrene, polyesters, acrylic resins, epoxy resins, fluorine type resins, silicone type resins, phenolic resins, vinyl resins, polyurethane, cellulose, chitin, chitosen, fibroin, keratin and natural rubbers.

* * * * *

UNITED STATES PATENT AND TRADEMARK OFFICE
CERTIFICATE OF CORRECTION

PATENT NO. : 5,223,244

DATED : June 29, 1993

INVENTOR(S) : Moro, et al.

It is certified that error appears in the above-indentified patent and that said Letters Patent is hereby corrected as shown below:

Col. 18, line 23       Delete " n-pentene " and substitute -- n-pentane --

Col. 18, lines 47-48   Delete " plyamides " and substitute -- polyamides --

Signed and Sealed this

Fifteenth Day of November, 1994

Attest:

BRUCE LEHMAN

*Attesting Officer*    *Commissioner of Patents and Trademarks*